United States Patent
Disch (10) Patent No.: US 9,360,417 B2
(45) Date of Patent: Jun. 7, 2016

(54) GAS MEASUREMENT DEVICE

(71) Applicant: SICK AG, Waldkirch (DE)

(72) Inventor: Rolf Disch, Waldkirch (DE)

(73) Assignee: SICK AG, Waldkirch (DE)

( * ) Notice: Subject to any disclaimer, the term of this patent is extended or adjusted under 35 U.S.C. 154(b) by 245 days.

(21) Appl. No.: 14/179,050

(22) Filed: Feb. 12, 2014

(65) Prior Publication Data

US 2014/0245816 A1 Sep. 4, 2014

(30) Foreign Application Priority Data

Feb. 25, 2013 (EP) ...................... 13156530

(51) Int. Cl.
*G01N 21/3504* (2014.01)
*G01N 21/17* (2006.01)

(52) U.S. Cl.
CPC ........ *G01N 21/3504* (2013.01); *G01N 21/1702* (2013.01); *G01N 2021/1704* (2013.01)

(58) Field of Classification Search
CPC .................. G01N 2021/1704; G01N 21/1702; G01N 21/3504
See application file for complete search history.

(56) References Cited

U.S. PATENT DOCUMENTS

| | | | |
|---|---|---|---|
| 4,457,162 A | 7/1984 | Rush et al. | |
| 5,357,340 A | 10/1994 | Zochbauer | |
| 2003/0209669 A1 | 11/2003 | Chou | |
| 2004/0145741 A1 | 7/2004 | Cole et al. | |
| 2011/0296900 A1* | 12/2011 | Thorson | G01N 21/1702 73/24.02 |
| 2015/0092194 A1* | 4/2015 | Waldmann | G01N 21/3504 356/454 |

FOREIGN PATENT DOCUMENTS

| | | |
|---|---|---|
| DE | 10 2005 049 522 B3 | 6/2007 |
| WO | 93/09422 A1 | 5/1993 |
| WO | 2007/054751 A1 | 5/2007 |

OTHER PUBLICATIONS

Kuhn, K.; Siegwart, M.; Pignanelli, E.; Sauerwald, T.; Schutze, A., "Versatile infrared gas measurement system with tunable microstructured Fabry-Pérot Filter," in Instrumentation and Measurement Technology Conference (I2MTC), 2012 IEEE International, pp. 1938-1943, May 13-16, 2012.*
Uotila, J., "Comparison of infrared sources for a differential photoacoustic gas detection system", Infrared Physics & Technology, www.sciencedirect.com, 51, pp. 122-130, (2007).
Koskinen, V., "Cantilever enhanced photoacoustic detection of carbon dioxide using a tunable diode laser source", Appl. Phys. B 86, pp. 451-454, (2007).
European Search Report in the counterpart Application No. 13156530.1, dated Aug. 5, 2013.

* cited by examiner

*Primary Examiner* — Lisa Caputo
*Assistant Examiner* — Punam Roy
(74) *Attorney, Agent, or Firm* — Nath, Goldberg & Meyer; Jerald L. Meyer; Rury L. Grisham (57) ABSTRACT

A gas measurement device for measuring the concentration of a plurality of gas components by means of absorption measurement comprising a light source for infrared radiation (3) or a thermal radiator (4) as a light source (5), an optics (22) for bundling the light of the light source (5), a band pass filter (4) and a photoacoustic measurement cell (12) for measuring a plurality of gas concentrations, wherein a Fabry-Perot filter (6) is provided in front of the photoacoustic measurement cell (12) in addition to the band pass filter (4) for selecting the absorption spectra.

5 Claims, 7 Drawing Sheets

GAS MEASUREMENT DEVICE

The invention relates to a gas measurement device in accordance with the preamble of claim 1.

BACKGROUND

A gas sensor arrangement is known from DE 10 2005 049 522 B3 having a radiation apparatus, a gas measurement space, a detector apparatus and an evaluation apparatus, wherein the evaluation apparatus controls the radiation apparatus, records and evaluates the detector signals and determines the measured gas concentration in dependence on the output signal of the detector apparatus. The radiation apparatus has at least two measurement radiation sources and at least one reference radiation source which each irradiate the radiation in at least one absorption band of the gas to be detected, in the measurement band, and which irradiate the radiation in at least one spectral band not absorbing the measured gas, the reference band. The detector apparatus is configured such that it can receive the radiation, after its passage through the gas measurement space in a measurement band or in a reference band, independently with respective spatial and/or temporal separation, wherein the evaluation apparatus operates the radiation sources in accordance with a specific control algorithm and determines and compares the output signals of the detector apparatus in the measurement band and/or in the reference band on the switching on of one of the radiation sources or on a radiation source comparison, optionally compensates a possible aging of the gas sensor arrangement and determines the measured gas concentration.

Known infrared gas sensors, for example, have a broad-band radiation source, an absorption path or a gas measurement space, a wavelength-selective element, e.g. an optical band pass filter such as an interference filter, a Fabry-Perot interferometer or a grating and a radiation detector, for example a pyroelectric detector, a semiconductor detector or a thermophilic detector. The attenuation of the radiation arriving at the detector due to the absorption by the gas molecules is a measure for the concentration of the gas absorbing at the set wavelength. The wavelength-selective element can be arranged in front of and/or behind the gas measurement space.

The use of a wavelength-selective radiation source such as an LED or a laser in combination with non-wavelength-selective radiation receivers is likewise known.

The radiation absorption by gas molecules in the infrared range is also utilized in photoacoustic gas sensors. The radiation absorption results in a heating of the gas in the gas measurement space. The pressure change resulting from this is registered by means of an acoustic detector such as a microphone or by means of a pressure sensor.

SUMMARY

It is the object of the present invention to provide a gas measurement device which ideally manages without macroscopically mechanically movable parts and the wavelength to be examined or the frequency spectrum to be examined is continuously variable. A measurement speed should furthermore be increased. A further object comprises providing a gas measurement device which is suitable to determine concentrations of a plurality of measurement gases without parts such as filters having to be mechanically replaced.

The object is satisfied by a gas measurement device for measuring the concentration of a plurality of gas components by means of absorption measurement comprising a light source for infrared radiation, an optics for bundling the light of the light source, a broadband filter and a photoacoustic measurement cell for measuring a plurality of gas concentrations. A Fabry-Perot filter is provided in addition to the broadband filter and in front of the photoacoustic measurement cell for selecting the absorption spectra.

Since the gas measurement device in accordance with the invention manages almost without macroscopically mechanically moved parts, it is less prone to malfunction. Mechanically moved parts are subjected to wear by friction which has the result that the gas measurement device has to be serviced. The gas measurement is more robust and less expensive due to the lack of mechanically moved parts.

The Fabry-Perot filter comprises an optical resonator which is formed from two partially transmitting mirrors. An incident light beam is only transmitted by the Fabry-Perot filter when it corresponds to its resonance conditions. Other spectral ranges are almost completely eliminated. This is done by constructive or destructive interference of the part beams. The Fabry-Perot filter thereby acts as an optical filter. The wavelength which is to pass through the Fabry-Perot filter can be varied by a micromechanical displacement of the mirrors.

The transmitted wavelength of the light beam can be set variably by the use of the Fabry-Perot filter so that the photoacoustic measurement cell can be acted on by light of changing wavelength, whereby different absorption spectra of different gases of a gas mixture can be set after one another. The spectral wavelengths at which the different gases have an absorption can also be determined continuously in accordance with the invention.

The variable wavelengths of the light beam can be set very quickly by the Fabry-Perot filter, namely in the range of a few seconds, in particular in the range of a few milliseconds.

The Fabry-Perot filter is configured as a piezo-controlled Fabry-Perot filter, for example. The Fabry-Perot filter is in this respect designed as a microelectromechanical system. Such systems are also known by the abbreviation MEMS. The Fabry-Perot filter used in accordance with the invention can be controlled electrostatically or piezoelectrically, for example.

The broadband filter is necessary to eliminate higher order wavelengths. It is thus possible to limit the measurement only for a single order, namely the first order, of an absorption spectrum, whereby a precise and exact determination of the gas to be measured is made possible.

Only one single light source is provided in a further development of the invention. The gas measurement device can thereby be manufactured more less expensively.

In a further development, the photoacoustic measurement cell has a vibrating beam and an interferometer for measuring the deflection of the vibrating beam. The gas is heated in a very short time period due to the absorption of the light beams by the gas at a specific absorption spectrum, whereby a pulse-like pressure change of the gas takes place in the photoacoustic cell. This pressure change results in a deflection of the vibrating beam. The vibrating beam, which is also called a cantilever, comprises a silicon membrane, for example. The vibrating beam serves as an optical element for an interferometer. A deflection of the vibrating beam can be determined very precisely on the basis of the interference measurement with the aid of the interferometer.

In accordance with a further preferred embodiment, an optical pulse shaper is provided between the light source and the photoacoustic measurement cell. The light of the light source is modulated by the optical pulse shaper. Pulsed light is particularly preferably produced by the optical pulse shaper, whereby the absorption in the measurement gas takes place in cyclic form, whereby a vibrating behavior of the vibrating beam is improved, in particular when a resonance behavior is achieved by the pulse shaper. The optical pulse shaper is realized in the simplest case by a rotatable slit diaphragm or pinhole diaphragm, whereby a cyclic interruption of the light beam is achieved. Such optical pulse shapers are also called choppers.

The Fabry-Perot filter, however, preferably forms the optical pulse shaper itself. This means that the Fabry-Perot filter is set, on the one hand, as already mentioned, so that only a specific wavelength of the light can pass through. The Fabry-Perot filter is furthermore controlled cyclically so that the light can only pass through the Fabry-Perot filter at specific times in the cycle, whereby pulse-shaped light is produced at the outlet of the Fabry-Perot filter. The Fabry-Perot filter thereby has a dual function in accordance with the invention, whereby the apparatus is considerably simplified. The Fabry-Perot filter is controlled via a control unit with which a desired transmitted wavelength of the Fabry-Perot filter and the frequency as well as the pulse break ratio, with which the light is interrupted by the Fabry-Perot filter, is set.

In a further development of the invention, a dichroitic beam splitter is arranged between the light source and the photoacoustic measurement cell, wherein a first light portion which passes through the beam splitter is directly incident into the photoacoustic measurement cell and the light portion reflected by the beam splitter is conducted via deflection means into the photoacoustic measurement cell. The Fabry-Perot filter is arranged in front of the beam splitter to select a desired wavelength or to modulate the intensity of the light. It is possible by the aforesaid further development to measure a plurality of spectral components, although the spectral range required for this purpose is so large that the free spectral range of the Fabry-Perot filter is initially not sufficient. However, due to the dichroitic beam splitter, a plurality of orders, for example the first and second orders or the first and third orders, of the single Fabry-Perot filter are utilized and are supplied to the single photoacoustic measurement cell via the beam splitter and by means of deflection means which can be designed as deflection mirrors or deflection prisms. A respective optical pulse shaper is arranged for modulating the light beams after the dichroitic beam splitter. The optical pulse shape can, for example, also be realized by a chopper, with the chopper having a different number of slits over two different radii for the differing light beams.

In a further special embodiment, a second Fabry-Perot filter can be arranged between a deflection means and the photoacoustic measurement cell. It is thereby now possible that each light beam of the dichroitic beam splitter can be influenced by one respective Fabry-Perot filter. In each of the two light beams, the exact wavelength can be set by the respective Fabry-Perot filter; and in addition, the light modulation for each light beam can be set independently of one another by the respective Fabry-Perot filter. In accordance with this further development, an additional optical pulse former is dispensed with since the respective Fabry-Perot filter takes over the function of the optical pulse shaper.

The invention will also be explained in the following with respect to further advantages and features with reference to the enclosed drawing and to embodiments. The Figures of the drawing show in:

DESCRIPTION OF THE EMBODIMENTS

Different embodiments in which identical parts are provided with identical reference numerals are shown in the following Figures. Features of the different embodiments can be combined with one another.

Figure 1:
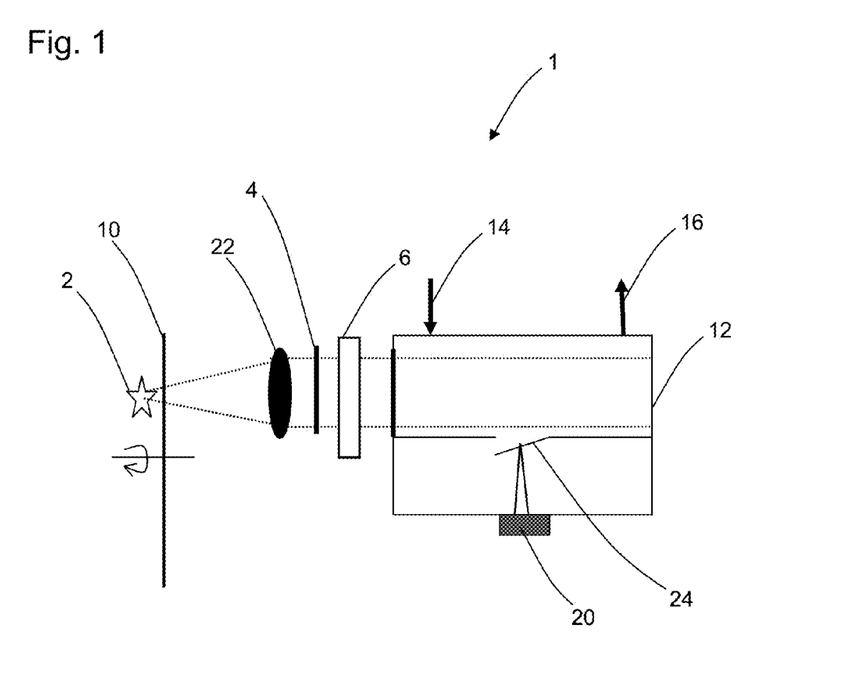
FIG. 1 a gas measurement device in accordance with a first embodiment.

FIG. 1 shows a gas measurement device 1 for measuring the concentration of a plurality of gas components by means of absorption measurement comprising a light source 2 for infrared radiation (thermal radiators). Furthermore, an optics 22 for bundling the light of the light source 2, a bandpass filter 4 and a photoacoustic measurement cell 12 for measuring the gas concentrations of a plurality of components are provided. A Fabry-Perot filter 6 is provided in addition to the band pass filter and preferably between the band pass filter 4 and the photoacoustic measurement cell 12 for selecting a wavelength to take an absorption spectrum. The photoacoustic measurement cell 12 has a gas inlet 14 and a gas outlet 16.

In this respect, the light source 2 transmits infrared light (thermal radiator). The photoacoustic measurement cell 12 is filled with a gas to be examined. Infrared radiation is only absorbed when gases are present in the measurement volume which absorb at the selected spectral wavelengths. This results in a heating and thus in a pressure increase in the measurement cell. This pressure increase results in a deflection of a vibrating beam 24 which is configured as a membrane, in particular as a silicon membrane. Such a membrane is also, as already mentioned, called a cantilever. The deflection of the membrane is in turn determined very precisely by an interferometer 20, with the deflection being proportional to the concentration of the measurement gas in the measurement volume of the photoacoustic measurement cell 12.

The spectral positions of the gas components without macroscopically moved mechanical components are set and are optionally also continuously determined with the aid of a Fabry-Perot filter 6, in particular of a piezo-controlled Fabry-Perot filter 6 or of a Fabry-Perot filter 6 in a micromechanical construction design which is electrostatically or piezoelectrically controlled. The variation and setting of the spectral wavelengths take place in seconds down to a few milliseconds.

A band pass filter 4 is provided to mask higher order interferences. In accordance with the first embodiment in accordance with FIG. 1, wavelengths can be set from 4.3 μm to 7.4 μm to measure the gas components CO, NO, SO2, NO2, N20, CO2 and H2O by means of only one single Fabry-Perot filter 6. Many different hydrocarbons can, for example, be measured using the design in accordance with FIG. 1 in the wavelength range from 3 μm to 3.8 μm. In accordance with this embodiment, all the gas components can be measured whose absorption bands are within the set free spectral range of the Fabry-Perot filter 6. The additional measurement and addition of further gas components is possible very simply when they have absorption bands within the Fabry-Perot filter 6.

The intensity of the light is modulated in this embodiment using an optical pulse shaper 10, in particular a rotatable slit disk, also called a chopper. The gas in the photoacoustic measurement cell 12 will then absorb in accordance with the modulation, which results in a periodic deflection of the vibrating beam 24. The vibration of the vibrating beam 24 is determined via the interferometer 20, with the deflection, as described above, being a measure for the concentration.

Figure 2:
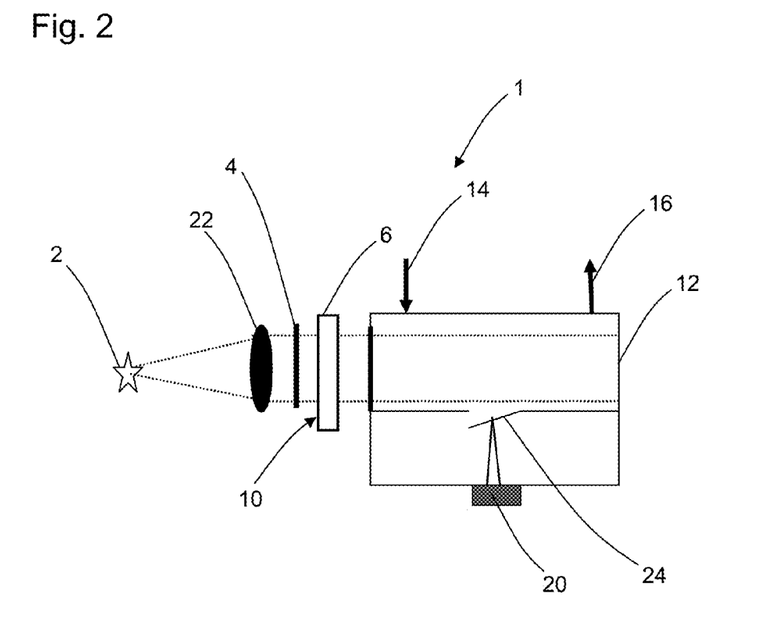
FIG. 2 a gas measurement device in accordance with a second embodiment.

FIG. 2 shows a similar design to FIG. 1, with the difference that the optical pulse shaper 10 is not provided as a separate assembly. In this case, the transmission peak of the Fabry-Perot filter 6 is periodically displaced outside the band pass filter 4 without a transmission for a higher order appearing so that the function of the optical pulse shaper 10 is emulated by the Fabry-Perot filter 6 in combination with the band pass filter 4. The Fabry-Perot filter 6 can thereby satisfy a dual function in accordance with the invention, namely the spectral selection of individual wavelength ranges and additionally the function of the optical pulse shaper 10; and the mechanical chopper can be dispensed with.

Figure 3:
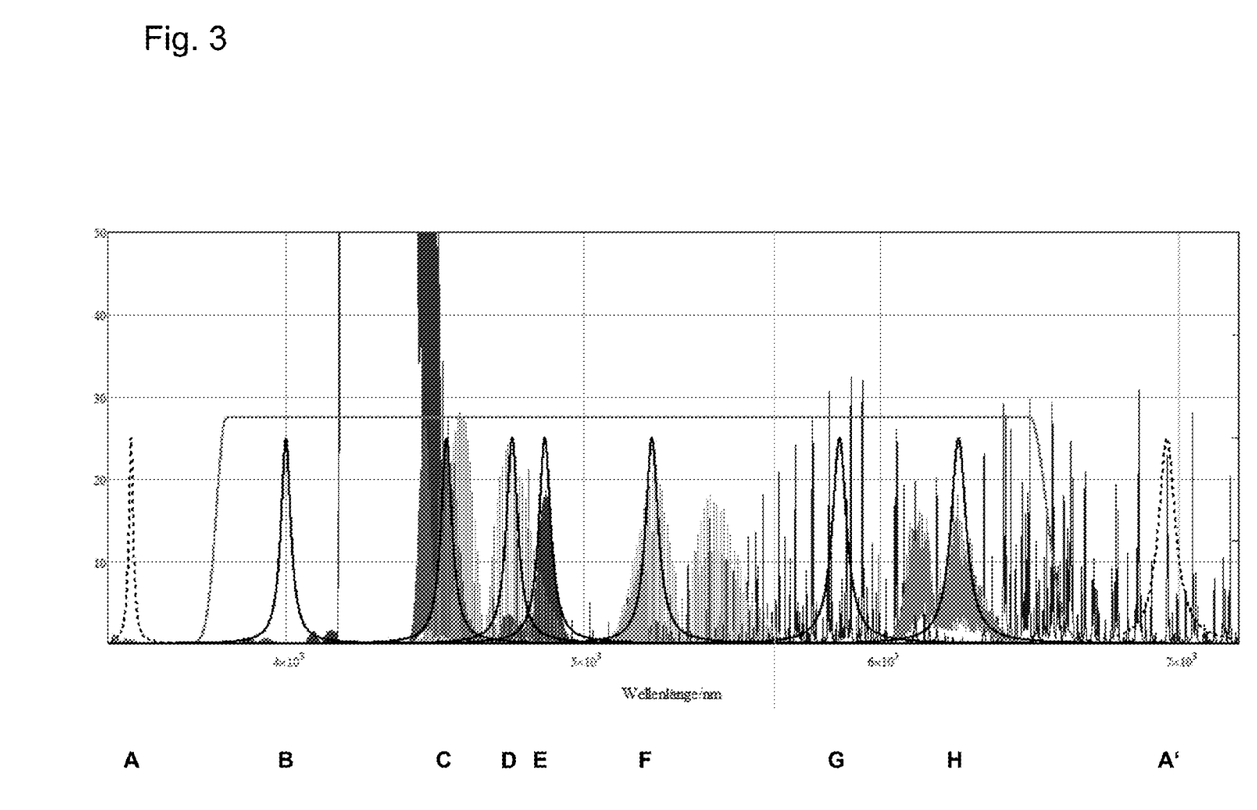
FIG. 3 an exemplary measuring configuration for different measurement gases.

FIG. 3 shows by way of example a possible measurement configuration for the components N2O, CO, NO, NO2, CO2, H2O, that is the absorption spectra of these components in one common image. The individual absorption spectra, which are shown by thin lines, are scaled as desired. The absorption bands shown belong to the named components, with the bands also partly overlapping. The spectral positions of the likewise idealized Fabry-Perot filter transmission peaks which are meaningful for measuring the components are shown by thick lines and the reference numerals A to H and A'. Position A is a dark position. Position D is above a CO absorption; position F above an NO absorption, etc. A possible measurement strategy would be as follows: Positions B to H are set after one another, for example at a time interval or a time pattern of a second and thus the respective matching wavelengths are selected to measure the individual components. The pulse shaping required for the measurement takes place by traveling to the position A or A' in the time interval or time pattern of a millisecond, whereby optical pulses are produced and the measurement can take place according to the above-described principle.

Figure 4:
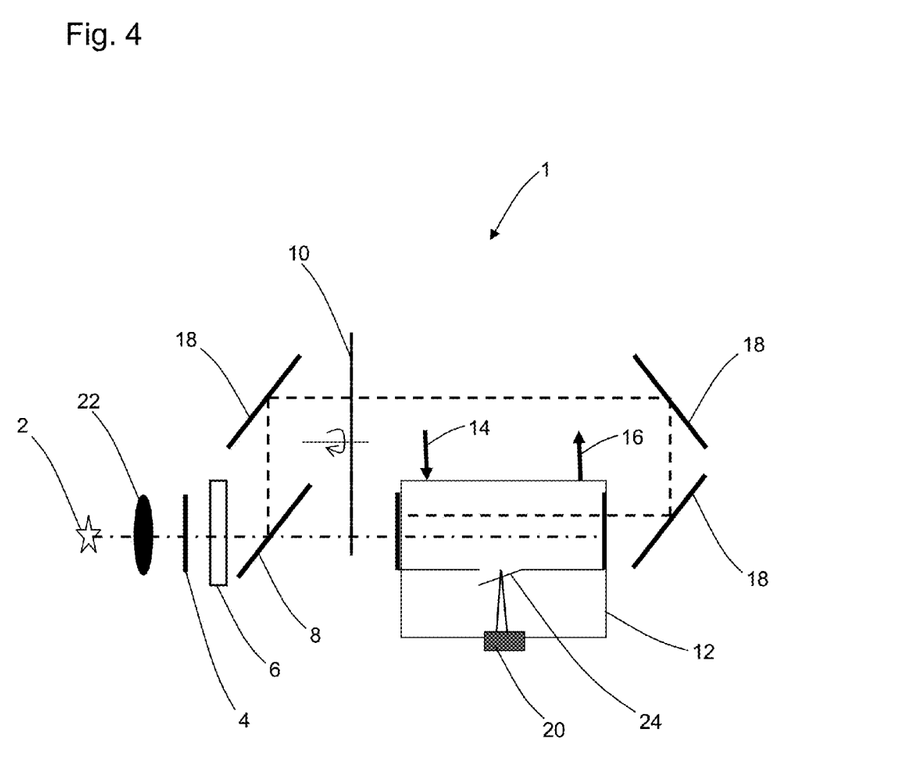
FIG. 4 a gas measurement device in accordance with a third embodiment.

FIG. 4 shows a further embodiment with the light source 2 and a downstream optics 22 for beam shaping. The band pass filter 4 is arranged after the optics 22. The light filtered by the band pass filter 4 further penetrates the Fabry-Perot filter 6 which here again serves to transmit an adjustable wavelength. The light filtered by the Fabry-Perot filter 6 is then incident on a dichroitic beam splitter 8 which splits the light beam into two different wavelengths. A first light beam passing through the dichroitic beam splitter 8 is modulated by an optical pulse shaper 10 (chopper) before this light beam then enters into the photoacoustic measurement cell 12. The second light beam, which is reflected by the dichroitic beam splitter 8, likewise enters into the photoacoustic measurement cell 12 via three deflection means 18 which respectively deflect the light beam by 90 degrees. The deflection means 18 can be configured, for example, as a deflection mirror 19 or as a deflection prism.

It is possible by the aforesaid further development in accordance with FIG. 4 to measure a plurality of spectral components, although the spectral range required for this purpose is so large that the free spectral range of the Fabry-Perot filter 6 is actually not sufficient. A plurality of orders, for example the first and second orders or the first and third orders, of the Fabry-Perot filter 6 are now utilized by the dichroitic beam splitter 8. The design in accordance with FIG. 4 is provided so that the measurement can only be carried out with one single photoacoustic measurement cell 12. The two frequency spectra or wavelength spectra of the different orders are separated with the aid of the dichroitic beam splitter 8, for example from 2.9 μm to 4.2 μm for an optical path of a shorter wavelength and from 4.4 μm to 7.7 μm for an optical path of a longer wavelength. A band pass filter 4 may also still be necessary here independently of the quality of the dichroitic beam splitter 8.

To be able also to separate the two spectral ranges on the two optical paths in a technical measurement using the only detection device (measurement cell 12), a (different) optical pulse shaper 10 is provided which is again configured as a chopper, but now has a different number of slits over two different radii. The portion of longer wavelength can thus e.g. be modulated at 1 kHz, for example, and the portion of shorter wavelength at greater than 2 kHz. The Fabry-Perot filter 6 can, for example, also be continuously determined in addition to the named embodiments. The signal evaluation takes place using an evaluation unit such as already described with reference to FIGS. 1 and 2 by the vibrating beam 24 and the interferometer 20 by means of a lock-in technique.

Figure 5:
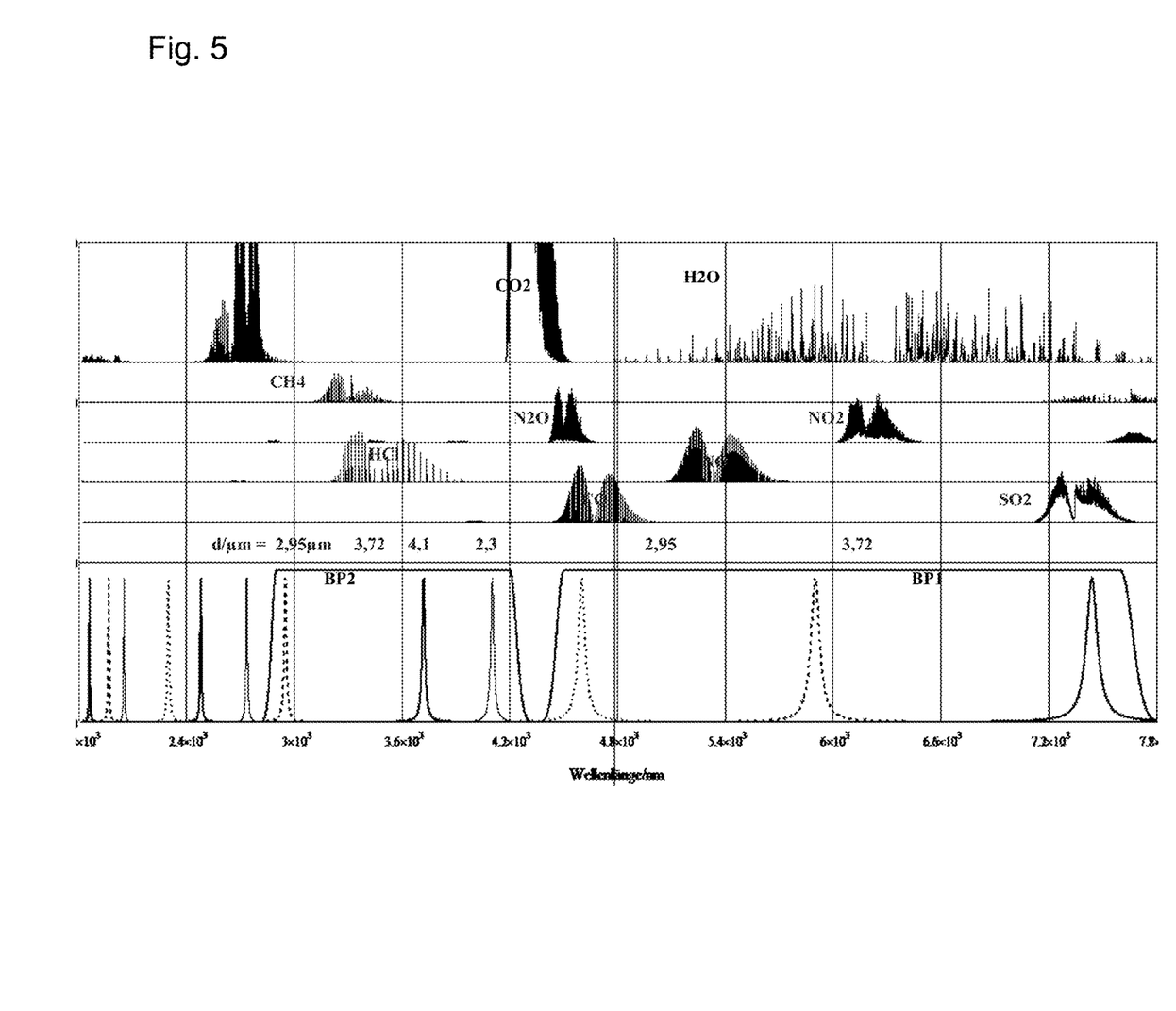
FIG. 5 a qualitative representation of absorption spectra in accordance with a further embodiment.

In FIG. 5, the spectral relationships are shown, namely the qualitative absorption spectra, for a measurement using an apparatus in accordance with FIG. 4, with two band passes BP1 and BP2 being used in contrast to FIG. 4. The two band passes BP1 and BP2 are selected so that several orders do not appear in the individual band pass filters. The individual absorption spectra of the different gases are provided with offsets for better clarity. In this configuration, the components CO, NO, NO2, SO2, CO2 and H2O can be measured in the longwave range at a lock-in frequency f1 and a number of hydrocarbons, CH4 is shown by way of example here, as well as HCl in the shortwave range at a lock-in frequency f2. At approximately 4 μm, the zero point signal is measured since absorptions can be neglected at this wavelength.

Some transmission curves of the Fabry-Perot filter 6 are shown in the lower graph region for different spacings of the mirrors of the Fabry-Perot filter. Both H2O, that is water, and CO2 can also be measured between 1800 nm and 2200 nm, in particular when the HO absorption becomes too large with the modulated infrared radiation, in that the third order is used for this purpose.

Figure 6:
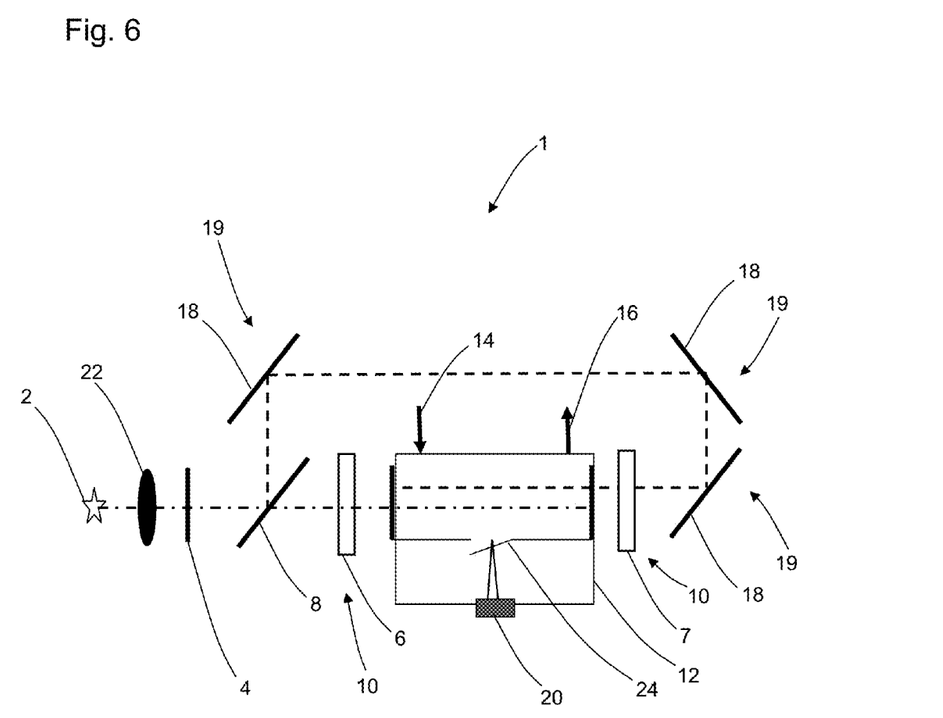
FIG. 6 a gas measurement device in accordance with a fourth embodiment.

In a further embodiment in accordance with FIG. 6, a second Fabry-Perot filter 7 is arranged between a deflection means 18 or a deflection mirror 19 and the photoacoustic measurement cell 12. It is thereby now possible that each part light beam of the dichroitic beam splitter 8 can be influenced by a respective one Fabry-Perot filter 6 or 7 respectively. This arrangement is sensible when the spectral ranges cannot be ideally separated.

FIG. 6 shows the light source 2 and the downstream optics 22 for beam shaping. The band pass filter 4 is arranged after the optics 22. The light filtered through the band pass filter 4 is further incident on the dichroitic beam splitter 8 which splits the light beam into two part beams each having different wavelength regions. The part light beam transmitted by the dichroitic beam splitter 8 is incident on the first Fabry-Perot filter 6 which serves to transmit an adjustable wavelength. The transmitted part light beam is also modulated by the first Fabry-Perot filter 6 as an optical pulse shaper 10 before this part light beam enters into the photoacoustic measurement cell 12. The second part light beam which is reflected by the dichroitic beam splitter moves via three deflection means 18, which deflect the light beam by 90 degrees in each case, onto the second Fabry-Perot filter 7 which sets a second wavelength. The reflected and deflected part light beam which passes through the second Fabry-Perot filter 7 is likewise modulated by the second Fabry-Perot filter 7 as an optical pulse shaper 10 before this part light beam then likewise enters into the single photoacoustic measurement cell 12. The deflection means 18 can be configured, for example, as a deflection mirror 19 or as a deflection prism.

In turn only a single photoacoustic measurement cell 12 is used. Furthermore, an additional mechanical optical pulse shaper, that is a chopper, is dispensed with. The individual spectral positions are set step-wise or continuously by the two provided Fabry-Perot filters 6 or 7 and are additionally displaced by different frequencies outside the spectral range of the associated band pass filter 4 in order also here simultaneously to realize a wavelength selection as well as the function of the optical pulse shaper. A band pass filter 4 can here also still be required between the beam splitter 8 and the light source 2 depending on the quality of the dichroitic beam splitter 8.

The signal evaluation or signal separation also takes place in this embodiment by means of the vibrating beam 24, the photoacoustic measurement cell 12 and the interferometer 20, as already described.

Figure 7:
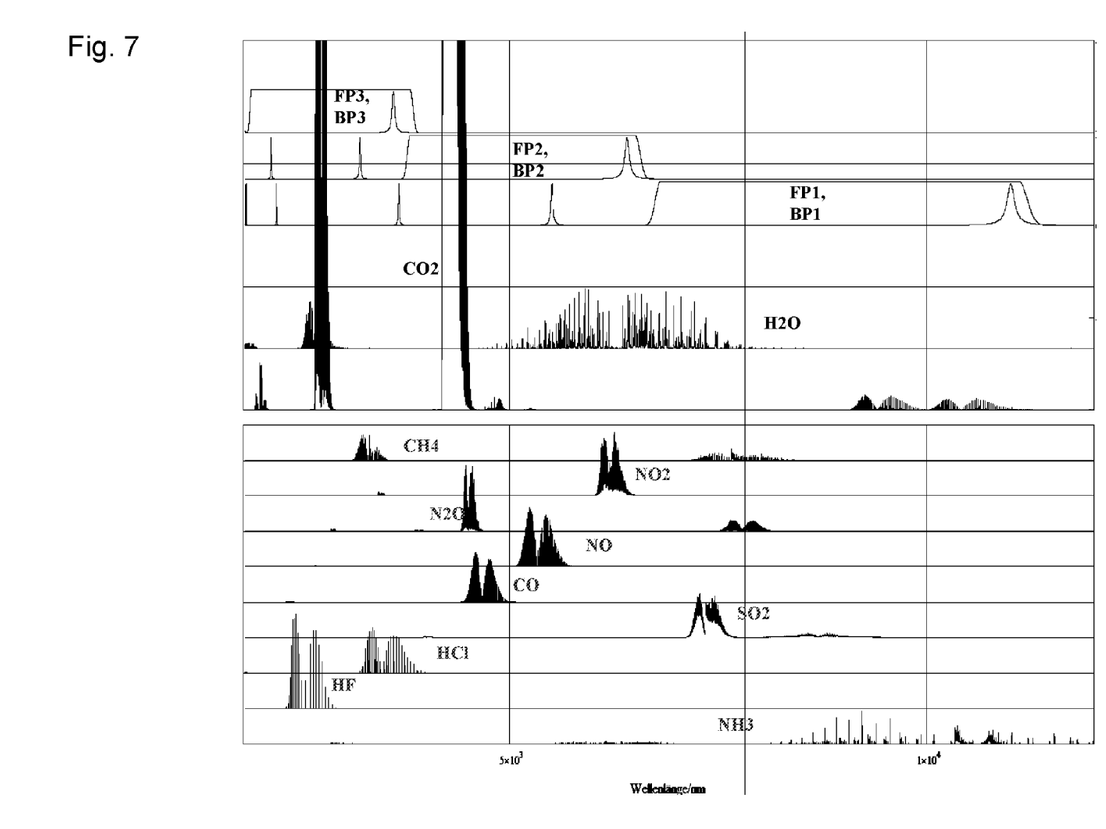
FIG. 7 a qualitative representation of absorption spectra in accordance with a further embodiment.

Which gas components can be measured in which configuration using the apparatus from FIG. 6 is shown by way of example in FIG. 7. The individual absorption spectra of the gases are provided with offsets for better clarity. The gas components NH3, CO2, SO2, H2O can be measured, for example, using one of the Fabry-Perot filters in a longwave range FP!, and N2O, CO, NO, NO2, CO2 and H2O can be measured in shortwave range FP2. The components HF and HCl can be measured in a wavelength range FP3. Other combinations are also provided which are also covered in this invention. It is important that the free spectral range of the individual Fabry-Perot filters is larger than the spectral range to be scanned. The band pass filters are shown in the embodiments in idealized form with transmission regions BP1, BP2 and BP3. They are set so that always only one order is detected. They are matched to the actual achievable reflection properties or transmission properties of the Fabry-Perot mirrors.

What is claimed is:

1. A gas measurement device for measuring the concentration of a plurality of gas components by means of absorption measurement, the device comprising: a light source (2) for infrared radiation, an optics (22) for bundling the light of the light source (2), a band pass filter (4), a photoacoustic measurement cell (12) for measuring gas concentrations, and a Fabry-Perot filter (6) arranged in front of the photoacoustic measurement cell (12) in addition to the band pass filter (4) for selecting the absorption spectra, wherein the photoacoustic measurement cell (12) has a vibrating beam (24) and an interferometer (20) for measuring the deflection of the vibrating beam (24).

2. The gas measurement device in accordance with claim 1, further comprising an optical pulse shaper (10) arranged between the light source (2) and the photoacoustic measurement cell (12).

3. The gas measurement device in accordance with claim 2, wherein the optical pulse shaper (10) is formed by the Fabry-Perot filter (6).

4. The gas measurement device in accordance with claim 1, further comprising a dichroitic beam splitter (8) arranged between the light source (2) and the photoacoustic measurement cell (12), wherein a first light portion which is incident through the beam splitter (8) is directly incident into the photoacoustic measurement cell (12) and the reflected light portion of the beam splitter (8) is conducted via deflection means (18) into the photoacoustic measurement cell (12).

5. The gas measurement device in accordance with claim 3, further comprising a second Fabry-Perot filter (7) arranged between a deflection means (18) and the photoacoustic measurement cell (12).

* * * * *